US006764857B2

(12) United States Patent
Allen et al.

(10) Patent No.: US 6,764,857 B2
(45) Date of Patent: Jul. 20, 2004

(54) SYSTEMS AND METHODS FOR MEASURING NITRATE LEVELS

(75) Inventors: George A. Allen, Swampscott, MA (US); Petros Koutrakis, Weston, MA (US); Yiming Ding, Malden, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/267,807

(22) Filed: Oct. 9, 2002

(65) Prior Publication Data

US 2003/0040120 A1 Feb. 27, 2003

Related U.S. Application Data

(63) Continuation of application No. 09/687,190, filed on Oct. 12, 2000, now Pat. No. 6,503,758.
(60) Provisional application No. 60/158,861, filed on Oct. 12, 1999.

(51) Int. Cl.[7] .............................................. G01N 33/00
(52) U.S. Cl. ......................... 436/110; 422/83; 422/88; 436/106; 436/115
(58) Field of Search ................................ 436/110, 106, 436/115, 113, 148, 116, 172; 422/83, 88, 55, 61, 52; 72/863.22; 250/339

(56) References Cited

U.S. PATENT DOCUMENTS

| | | | | |
|---|---|---|---|---|
| 4,236,895 A | * | 12/1980 | Stahl | 436/116 |
| 4,647,777 A | * | 3/1987 | Meyer | 250/339.11 |
| 5,401,468 A | * | 3/1995 | Patashnick et al. | 422/80 |
| 5,854,077 A | * | 12/1998 | Wolfson et al. | 436/110 |
| 5,970,804 A | * | 10/1999 | Robbat, Jr. | 73/863.12 |
| 5,983,732 A | * | 11/1999 | Hering et al. | 73/863.22 |

OTHER PUBLICATIONS

Yamamoto and Kosaka; "Determination of Nitrate in Deposited Aerosol Particles by Thermal Decomposition and Chemiluminescence", Anal. Chem. 66: 362–367, (1994).
Liu et al.; "Real–Time Monitoring of Particulate Nitrate in the Proposphere", Department of Chemistry, University of California, Riverside, CA 92521.
Noble and Prather; "Real Time Measurement of Correlated Size and Composition Profiles of Individual Atmospheric Aerosol Particles", Environment Science and Technology, 30(9): 2667–2680 (1996).
Kalystov et al.; "The Steam–Jet Aerosol Collector", Atmospheric Environment, 29(17): 2229–2234, (1995).
Appel et al; "Simultaneous Nitric Acid, Particulate Nitrate and Acidity Measurements in Ambient Air", Atmospheric Environment 14: 349–354, (1980).
Navas et al.;"Air Analysis: Determination of Notrogen Compounds by Chemiluminescence", Atmospheric Environment 31(21): 3603–3608, (1997).

(List continued on next page.)

Primary Examiner—Jill Warden
Assistant Examiner—Sam P. Siefke
(74) Attorney, Agent, or Firm—Dana M. Gordon; Foley Hoag LLP (57) ABSTRACT

The systems and methods described herein relate to the measurement of nitrate levels in a sample of gas, for example, air, exhaust, or other sources of gas. Moreover, the systems and methods described herein are capable of operating using short sample collection periods, permitting rapid data collection and finely time-resolved nitrate monitoring over a span of time. Additionally, ambient nitrate can effectively be distinguished from other airborne particles, such as sulfate and carbon.

17 Claims, 5 Drawing Sheets

OTHER PUBLICATIONS

Liu et al.; "An Electrostatic Micro–Collection Interface for Aerosol Collection. Automated Ion Chromatographic Analysis of Aerosols", Talanta, 43:1681–1688, (1996).

Simon et al; "Continuous Automated Measurement of Gaseous Nitrous and Nitrite and Nitrate", Environment Science Technology 29: 1534–1541 (1995).

Simon and Dasgupta; "Continuous Automated Measurement of the Soluble Fraction of Atmospheric Particulate Matter", Anal. Chem. 67:71–78, (1995).

Buhr et al.; "Development of a Semi–Continuous Method for the Measurement of Nitric Acid Vapor and Particulate Nitrate and Sulfate", Atmospheric Environment 29(19): 2609–2624, (1995).

* cited by examiner

SYSTEMS AND METHODS FOR MEASURING NITRATE LEVELS

This application is a continuation of U.S. application Ser. No. 09/687,190, filed Oct. 12, 2000 now U.S. Pat. No. 6,503,758, which application claims priority to U.S. Provisional Application No. 60/158,861, filed Oct. 12, 1999, both of which are hereby incorporated herein by reference.

BACKGROUND OF THE INVENTION

Particulates are tiny clumps of soot, dirt, and various chemicals that have been linked to a wide variety of health problems—asthma, and higher rates of disease affecting the cardiovascular system or lungs. Since 1987, EPA standards have governed all particulates under 10 micrometers in diameter. This category of particulate matter is called PM10. Recently, however, studies have suggested that the most dangerous particles are actually the smaller ones, which penetrate deeper in the lungs' aereoles. Thus, new regulations will build in a separate standard for particles less than 2.5 micrometers in diameter—PM2.5.

While PM10 contains a lot of wind-blown soil, PM2.5 is derived mainly from burning fossil fuels. PM2.5 typically contains a mixture of elemental carbon, organic carbon, sulfate and nitrate particles, and acid droplets. It is unlikely that all components of PM2.5 contribute equally to the observed health effects, yet the present lack of sufficient data quantifying the individual components prevents the EPA from separately regulating these components. Because regulating PM2.5 collectively is not a cost-effective solution, the agency is under great scientific, industrial, and political pressure to specifically identify sources of the observed particle health-effects. Thus, interest in measuring the individual components of PM2.5 has increased dramatically over the last few years.

A number of methods are known for measuring atmospheric nitrate levels. Koutrakis et al., Environ. Sci. Technol. 22:1463, 1988 disclose an integrated sampling method (Harvard/EPA Annular Denuder System (HEADS)) which is designed to measure various atmospheric components including particulate nitrate. The method provides a non-quantitative conversion of particulate nitrate to nitric acid vapor by collection of atmospheric fine particles on a Teflon filter, with a sodium carbonate-coated filter downstream to collect nitric acid vapor produced by volatization of ammonium nitrate and by the reaction of ammonium nitrate with acidic sulfate particles.

Wendt et al., "Continuous monitoring of atmospheric nitric oxide and nitrogen dioxide by chemiluminescence" in Methods of Air Sampling and Analysis, editor, J. P. Lodge Jr., Lewis Publishers, Chelsea, Mich., pp 415–421 (1989), disclose a continuous chemiluminescent $NO_x$ detection method. Yamamoto et al., Anal. Chem., 1994, 66, 362–367, describe a nitrate analysis method relying on chemiluminescent $NO_x$ detection. $NO_x$ generally refers to $NO_2$ and NO taken together.

Brauer et al., Environ. Sci. Technol. 24:1521, 1990 disclose a method for the continuous measurement of nitrous acid and nitric acid vapors which does not distinguish between the two species. Klockow et al., Atmospheric Environment, 1989, 23, 1131–1138, disclose thermodenuder systems for the discontinuous measurement of nitric acid vapor and ammonium nitrate. Buhr et al., Atmospheric Environment, 1995, 29, 2609–2624, teach a denuder for sampling nitric acid, nitrate, and sulfate. Wolfson et al., U.S. Pat. No. 5,854,077, present a continuous differential nitrate measurement method.

Many of these and other existing methods for nitrate measurement require labor-intensive, manual collection of 24-hour integrated samples and laboratory analysis of the collected components. Not only are such samples expensive to collect, but the lengthy collection period prevents the detection of cycles and patterns which occur over the course of a day. Convenient techniques which offer improved temporal resolution and are capable of unifying the collection and analysis processes are badly needed now to reveal these daily patterns, both for epidemiological research and for regulatory monitoring.

SUMMARY OF THE INVENTION

The systems and methods described herein relate to the measurement of nitrate in gas samples by collection and analyzing samples by a technique which permits a short cycling time. Thus, in one aspect, the invention provides a system for measuring nitrate levels having a sample inlet for receiving a sample of gas, a collection body coupled to said sample inlet, a filter mounted within said body to collect particles from said sample of gas, a heater coupled to the body to heat the body, a gas inlet coupled to said body to provide a flow of gas through said body, and a detector coupled to said body to measure an $NO_x$ concentration. In a certain embodiment, the system further comprises a source of gas coupled to said gas inlet. The gas may be nitrogen or another gas which is substantially free of oxygen.

In another embodiment, the system also includes a catalyst, coupled to said body and to said detector, capable of reducing $NO_2$ to NO. The catalyst may comprise molybdenum, carbon, or ferrous sulfate.

In certain embodiments, the detector included in the system has a light sensor, and may further include an ozone generator, for example, for the detection of the chemiluminescent oxidation of NO. In another embodiment, the detector includes an infrared sensor. In yet another embodiment, the detector includes a material which reversibly binds NO.

In one embodiment, the filter comprises quartz fibers.

In yet another embodiment, the system includes an extractor coupled to the sample inlet and to the collection body to substantially remove $NO_2$ from the gas sample. The extractor may comprise a hydroxyl-bearing solvent and a base, e.g., glycerol and an organic base, e.g., an amine, such as triethanolamine.

In yet another embodiment, the system also includes a selection platform, situated between the sample inlet and the extractor, to substantially remove particles larger than about 2.5 microns. The selection platform may be a filter, an inertial impactor, or any other suitable device.

In one embodiment, the system further includes a cooling system to cool the collection body.

In yet another aspect, the invention relates to a method for measuring a level of nitrate by receiving a gas sample, collecting nitrate particles from the gas sample on a filter, passing a stream of gas substantially free of oxygen over the collected particles, volatilizing the collected particles by heating to generate $NO_x$, and measuring a level of $NO_x$.

In one embodiment, the method further includes substantially removing $NO_2$ prior to collecting nitrate particles, e.g., by passing the received sample over a hydroxyl-bearing solvent and a base, e.g., an organic base such as triethanolamine.

In another embodiment, the method further includes removing particles larger than about 2.5 microns from the received gas sample, e.g., by passing the received sample through an inertial impactor or by passing the received sample through a filter.

In one embodiment of the method, passing a stream of gas includes passing a stream of nitrogen over the collected particles.

In yet another embodiment, the method further comprises reducing generated $NO_2$ to NO using a metal catalyst, e.g., by contacting the $NO_2$ with a molybdenum catalyst.

In certain embodiments, measuring a level of $NO_x$ includes reacting NO with ozone. In yet another embodiment, measuring a level of $NO_x$ includes detecting infrared absorption. In certain other embodiments, measuring a level of $NO_x$ includes adsorbing $NO_x$ on a conductive material.

In one embodiment, collecting nitrate particles comprises collecting nitrate particles on a filter comprising quartz fibers.

In another embodiment, volatilizing the collected particles includes rapidly heating the collected particles to at least 300° C.

In yet another aspect, the invention provides a system for measuring nitrate levels, including a sample inlet to receive a sample of gas, an extractor coupled to said sample inlet to substantially remove $NO_2$ from the gas sample, a collection body coupled to said sample inlet, an inertial impactor mounted within said body to collect particles from the gas sample, a current source coupled to the inertial impactor to heat the inertial impactor and generate $NO_x$ and a detector coupled to said catalyst to measure an $NO_x$ concentration.

In yet another aspect, the invention relates to a method for measuring a level of nitrate by receiving a gas sample, substantially removing $NO_2$ from the gas sample, collecting nitrate particles from the gas sample with an inertial impactor, passing a stream of gas substantially free of oxygen over the collected particles, volatilizing the collected particles by heating to generate $NO_x$ and measuring a level of $NO_x$ generated by the heated particles.

In yet another aspect, the invention provides a system for measuring nitrate levels having means for receiving a sample of gas, support means coupled to the means for receiving, means for collecting particles coupled to the support means, means coupled to the support means, for heating the support means to generate $NO_x$, means, coupled to the support means, for flowing a stream of gas through the support means, and means for measuring an $NO_x$ concentration coupled to the support means.

In one embodiment, such a system also includes means for substantially removing $NO_2$ from the sample of gas, coupled to said means for receiving and said support means.

In another embodiment, such a system further includes means for reducing $NO_2$ to NO, coupled to the support means and to the means for measuring.

In yet another aspect, the invention relates to a method of manufacturing a nitrate measurement apparatus by providing a sample inlet for receiving a sample of gas, coupling a collection body to the sample inlet, disposing a filter within the body, coupling a heater to the body, coupling a gas inlet to the body, and coupling an $NO_x$ detector to the body.

In one embodiment, the method further comprises disposing an $NO_2$ extractor between said sample inlet and said collection body.

In another embodiment, the invention further comprises disposing a catalyst capable of reducing $NO_2$ to NO between said collection body and said $NO_x$ detector.

BRIEF DESCRIPTION OF THE FIGURES

The following figures depict certain illustrative embodiments of the invention in which like reference numerals refer to like elements. These depicted embodiments are to be understood as illustrative of the invention and not as limiting in any way.

DETAILED DESCRIPTION OF THE ILLUSTRATED EMBODIMENTS

The description below pertains to several illustrative embodiments of the invention. Although many variations of the invention may be envisioned by one skilled in the art, such variations and improvements are intended to fall within the compass of this disclosure. Thus, the scope of the invention is not to be limited in any way by the disclosure below.

The systems and methods disclosed herein are useful for measuring nitrate levels, for example, in the atmosphere, and may be capable of performing sample collection and analysis within about ten minutes. Thus, variability of nitrate levels can be determined over relatively short intervals, e.g., for use in epidemiological studies, regulatory monitoring, or other research. Furthermore, the system can be assembled or manufactured using convenient, commercially available components.

Figure 1:
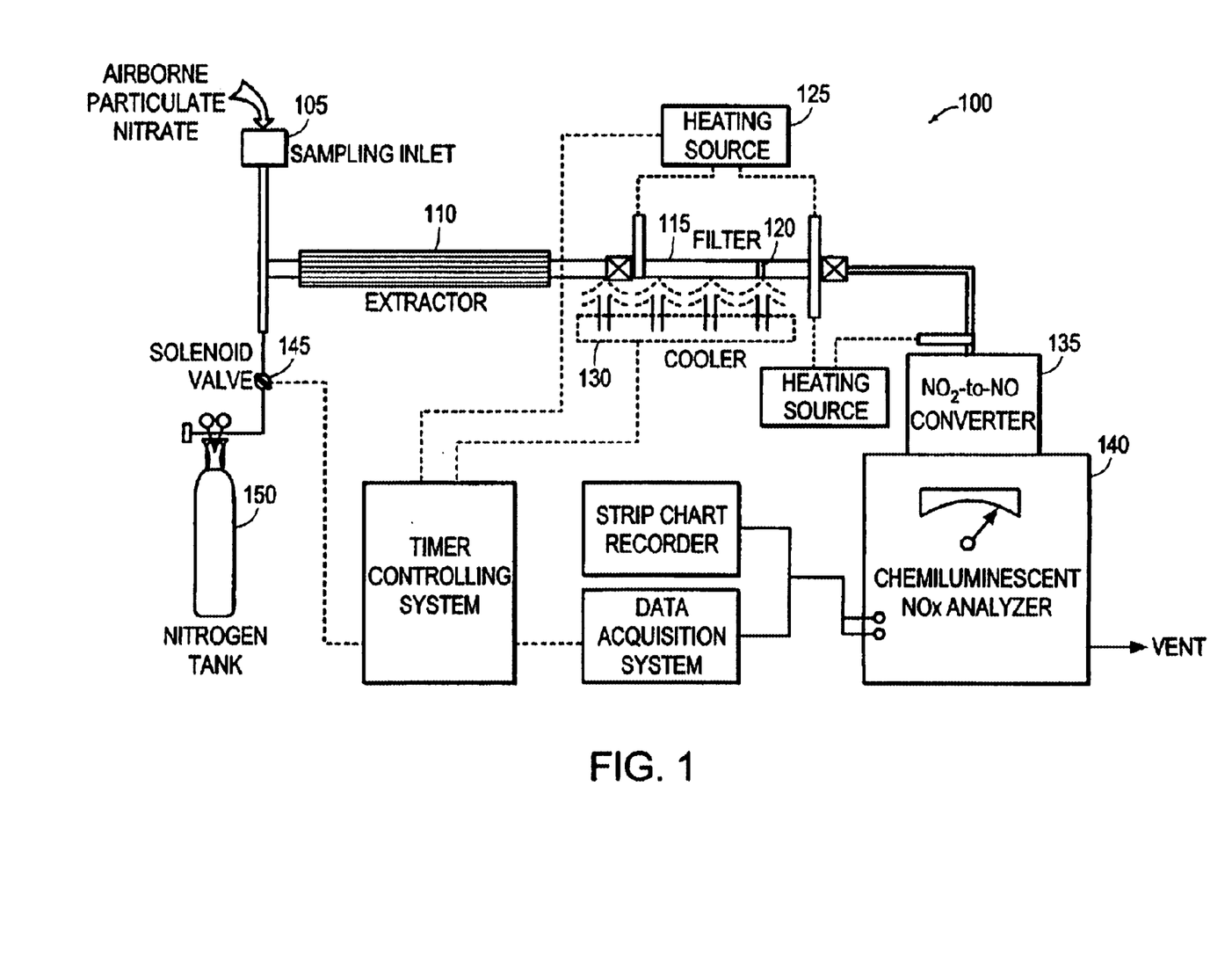
FIG. 1 depicts a system for measuring nitrate levels as described herein.

An exemplary system 100 for measuring nitrate levels is depicted in FIG. 1. The system 100 includes a sample inlet 105, an extractor 110, a collection body 115, a filter 120, a heater 125, a cooling system 130, a catalyst 135, a detector 140, a gas inlet 145, and a gas source 150. Other components, such as a control system, a data acquisition and recording system, or a second independent heater may optionally be included. Variations on the depicted system which are capable of functioning as described herein will be apparent to those of ordinary skill in the art and are intended to be encompassed by this disclosure.

A sample of gas, such as a sample of air or exhaust, may be received by the system using sample inlet 105. The sample of gas may be forced into the system 100, for example, by passing an exhaust stream through the system 100. Alternatively, the sample of gas may be drawn into the system 100 by a vacuum, e.g., by providing a vacuum beyond the detector 140, or by utilizing the Bernoulli effect, e.g., by passing a stream of gas rapidly past the inlet 105, e.g., using the gas inlet 145. The sample inlet 105 may include a selection platform for removing particles larger than about 2.5 microns, such as an inertial impactor or a filter, as is well known in the art. The sample of gas may then pass into the extractor 110 to remove contaminant gases. The extractor 110 may be a denuder, such as the honeycomb denuder described in U.S. Pat. No. 5,302,191 or an annular denuder, another diffusion denuder, or any other system known in the art for removing gases from a sample of gas. For example, the extractor 110 may include an acidic material, such as citric acid or sulfuric acid, to trap basic compounds, such as ammonia. In one embodiment, the extractor 110 is selected to remove at least 50%, or at least 90%, or even at least 95% of the gaseous $NO_2$ from the sample of gas, as gaseous $NO_2$ may introduce error into the nitrate measurement. Such an extractor may include a hydroxyl-bearing solvent, such as ethylene glycol, propylene glycol, glycerol, benzyl alcohol, or another hydroxylic solvent, and a base, including an inorganic base, such as a metal carbonate, bicarbonate, hydroxide, or phosphate, e.g., sodium hydroxide or potassium carbonate, and/or an organic base, such as an amine, e.g., 1,8-bis(dimethylamino)-naphthalene, diazabicyclooctane, diazabicyclononane, triethanolamine, diethanolamine, N,N-dimethyl-2-hydroxymethylaniline, or another organic base. In certain embodiments, the hydroxyl-bearing solvent and the organic base are selected to have low vapor pressures at atmospheric pressure, e.g., less than 50 Torr, or less than 10 Torr. Other systems for removing $NO_2$ or other selected contaminants are known in the art, and may be used alone or in any combination to remove any such compounds from the sample of gas.

The sample of gas may then pass into the collection body 115 and through filter 120. The filter 120 may then trap nitrate particles, in addition to other particles of similar size, e.g., about 2.5 microns or less, while allowing gaseous compounds to pass through. The collection body may be composed of any material capable of withstanding sufficient heat to perform the method as described herein, such as metal, ceramic, glass, quartz, or other heat-resistant material. For example, the collection body may be composed of steel, molybdenum, or an alloy comprising either material. The filter may be composed of any suitable material, e.g., quartz fibers, glass fibers, metal, or other material capable of withstanding temperatures sufficient to volatilize the trapped particles. A stream of gas substantially free of oxygen, e.g., including less than about 5% or less than about 1% oxygen, such as nitrogen gas, helium, or argon, may then be passed over the trapped particles. This procedure helps to reduce unwanted oxidation of ammonia or other low oxidation state nitrogen-containing compounds, such as ammonium sulfate, during heating. The gas may be introduced using gas inlet 145 from gas source 150.

The heater 125 may then heat the filter 120 or the collection body 115 to volatilize the trapped particles. The heater may perform this function by any means known in the art. For example, the heater 125 may generate heat itself, such as with a heating element, e.g., a nichrome wire or a heat lamp, used to heat the collection body or filter, or it may apply current to the filter 120 or the collection body 115 to heat that element by resistance, or it may heat the sample by any other means known in the art. In addition to heating the collection body 115 and/or the filter 120, the heater 125 or a second heater may heat all or a portion of the path between the collection body 115 and the catalyst 135. Upon volatilization, nitrate may be converted to species such as $HNO_3$, $NO_2$, and NO which are carried by the stream of gas to the catalyst 135.

In certain embodiments, for example, wherein an extractor 110 is not used to remove $NO_2$ from the gas sample, a portion of the gaseous $NO_2$ in the sample of gas may be adsorbed by material on the filter, such as soot or other particulate matter, rather than passing through the filter. Upon heating such $NO_2$ may be desorbed at a temperature below that at which nitrate begins to substantially volatilize. In such embodiments, it may be advantageous to heat the collection body 115 and filter 120 gradually in order to release this unwanted $NO_2$ prior to detection and measurement of the $NO_x$ species liberated by volatilization of nitrate. $NO_x$, as used herein, refers generally to NO and $NO_2$. By this method, more accurate nitrate determinations may be measured. Rapid heating, however, may permit more rapid cycling between collection and analysis phases. Similarly, cooling system 130 may cool the collection body 115 and/or filter 120 by any means, such as by passing an unheated fluid, e.g., air or water, over the exterior surface of the apparatus, to further enable more rapid cycling between collection and analysis phases. Thus, the speed of heating may be adjusted to balance cycling time with measurement accuracy, depending on the needs of a particular situation and the relative importance of accounting for $NO_2$ in the sample of gas.

The catalyst 135 may be any material, such as a molybdenum or carbon converter, ferrous sulfate, or any other material capable of reducing $NO_2$ to $NO_x$ as is known in the art. In embodiments where a detector 140 is used which is capable of simultaneously detecting $NO_2$ and NO, a catalyst 135 need not be included in the system, and the stream of gas may flow directly from the collection body 115 and filter 120 to the detector 140.

The detector 140 may be any component capable of detecting the amount of $NO_x$ in the stream of gas. A number of methods are known for detecting $NO_x$ in flowing gas streams. Perhaps the most well known and widely used process involves instruments using the chemiluminescent reaction of nitric oxide (NO) and ozone. The process operates by the reaction of ozone and nitric oxide within a reaction chamber having a transmissive window, allowing light produced by the chemiluminescent reaction to be monitored by a detector. Typical components using this process may be found in U.S. Pat. Nos. 3,967,933 to Etess et al.; 4,236,895 to Stahl; 4,257,777 to Dymond; 4,315,753 to Bruckenstein et al.; 4,657,744 to Howard; 4,765,961 to Schiff; and 4,822,564 to Howard. The use of a chemiluminescent nitrogen oxide monitoring device in controlling a nitrogen oxide removal unit placed on the outlet of a boiler is shown in U.S. Pat. No. 4,188,190 to Muraki et al. Because these systems are typically not capable of detecting $NO_2$ in the gas stream, a catalyst 135 may be employed in conjunction with such a detector.

Another procedure involves the use of an infrared beam, detector, and a comparator chamber. In U.S. Pat. No. 4,647,777 to Meyer, a beam of infrared light is passed through a gas sample and into a selective infrared detector. The beam is split and one portion passes through a chamber containing a fluid that absorbs the spectral wavelengths of the selected gas. The two beams are compared and the difference between the two beams gives an indication of the amount of a selected gas in the sample.

A semiconductor $NO_x$ sensor is described in U.S. Pat. No. 5,863,503. The resistance of this sensor is altered by the absorption of NO and $NO_2$. Such a detector 140 may thus simultaneously measure NO and $NO_2$ levels, and therefore may function accurately in the absence of a catalyst 135.

One of the above detectors, or any other detector capable of measuring NO or $NO_2$ concentrations, may be employed as detector 140. In the case of a detector which is capable of detection $NO_2$ but not NO, it may be advantageous to oxidize NO in the stream of gas to $NO_2$, for example, using an ozone generator or other source of oxidant. The detector 140 may include or may be coupled to a processor, plotter, or other recording apparatus for displaying, recording, or storing data collected by the detector 140.

In certain embodiments, the filter 120 may be replaced by an inertial impactor, which is also known to be useful for collecting particulate matter from a stream of gas. In order to volatilize the collected sample, the inertial impactor may be heated directly, or indirectly, as described above for a filter embodiment. Otherwise, the system is analogous to the system described above. Thus, in one embodiment, an inertial impactor is used in a system as described above which uses an $NO_2$ extractor, such as a diffusion denuder, as described above.

A system 100 as described above may be manufactured by coupling a sample inlet to a collection body, disposing a filter in said collection body, coupling said collection body to an $NO_x$ detector, and coupling a gas inlet to said body. In certain embodiments, the method may further include coupling an extractor, such as an $NO_2$ extractor as described above, between said sample inlet and said filter. When the detector employed does not adequately detect $NO_2$, a catalyst may be disposed between said detector and said collection body to reduce $NO_2$ to NO. Alternatively, if the detector employed does not adequately detect $NO_x$ an oxidizer may be disposed between said detector and said collection body. The components included in such a system may be any of the components set forth above or components that function equivalently or analogously.

The following examples are provided solely to further illustrate the nature and advantages of one embodiment of the present invention and are not intended to limit the scope of the invention in any way.

Exemplification

A system as described above and depicted in FIG. 1 was tested to determine the accuracy and utility of the measurements recorded thereby.

Figure 2:
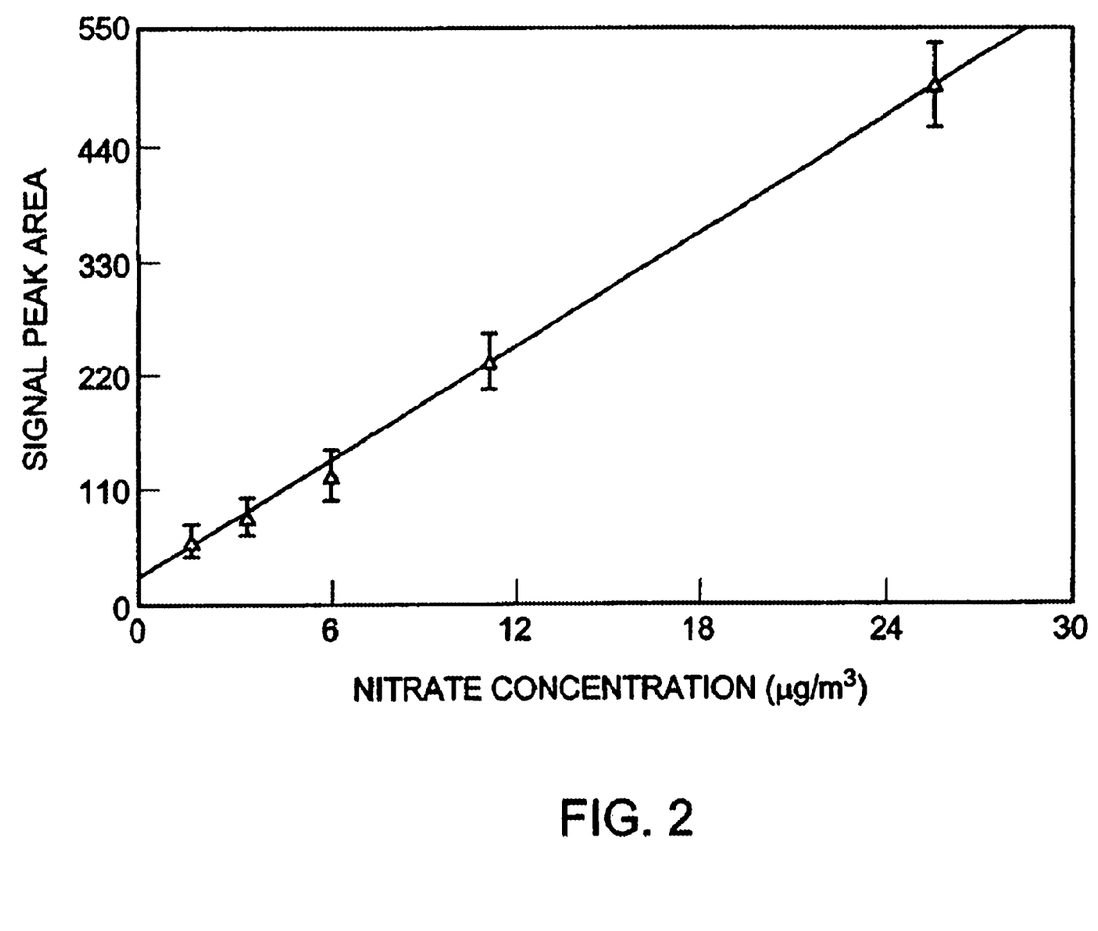
FIG. 2 illustrates the accuracy of a method for measuring nitrate levels as described herein.

FIG. 2 shows that as nitrate concentration in the gas sample increases, instrument response increases in turn. Furthermore, the very linear fit indicates that the instrument provides a linear response and should measure nitrate levels accurately over a broad range of concentrations.

Figure 3:
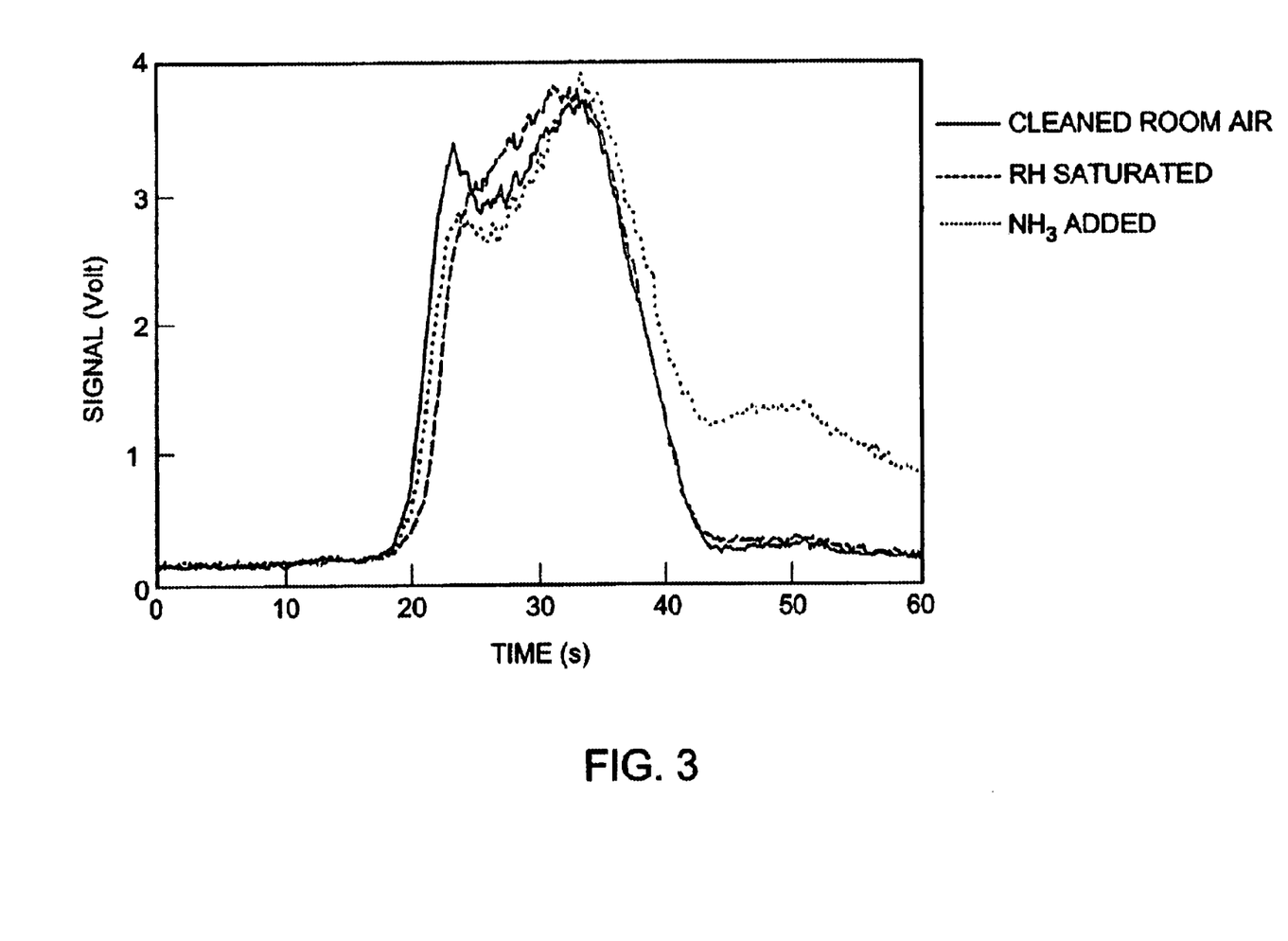
FIG. 3 shows the effect of atmospheric conditions on the method described herein.

FIG. 3 shows that the introduction of species, such as water (relative humidity (RH) saturated) or ammonia, into the sample of gas does not significantly affect the nitrate level readings of the instrument. In all cases, the peak area is relatively similar.

Figure 4:
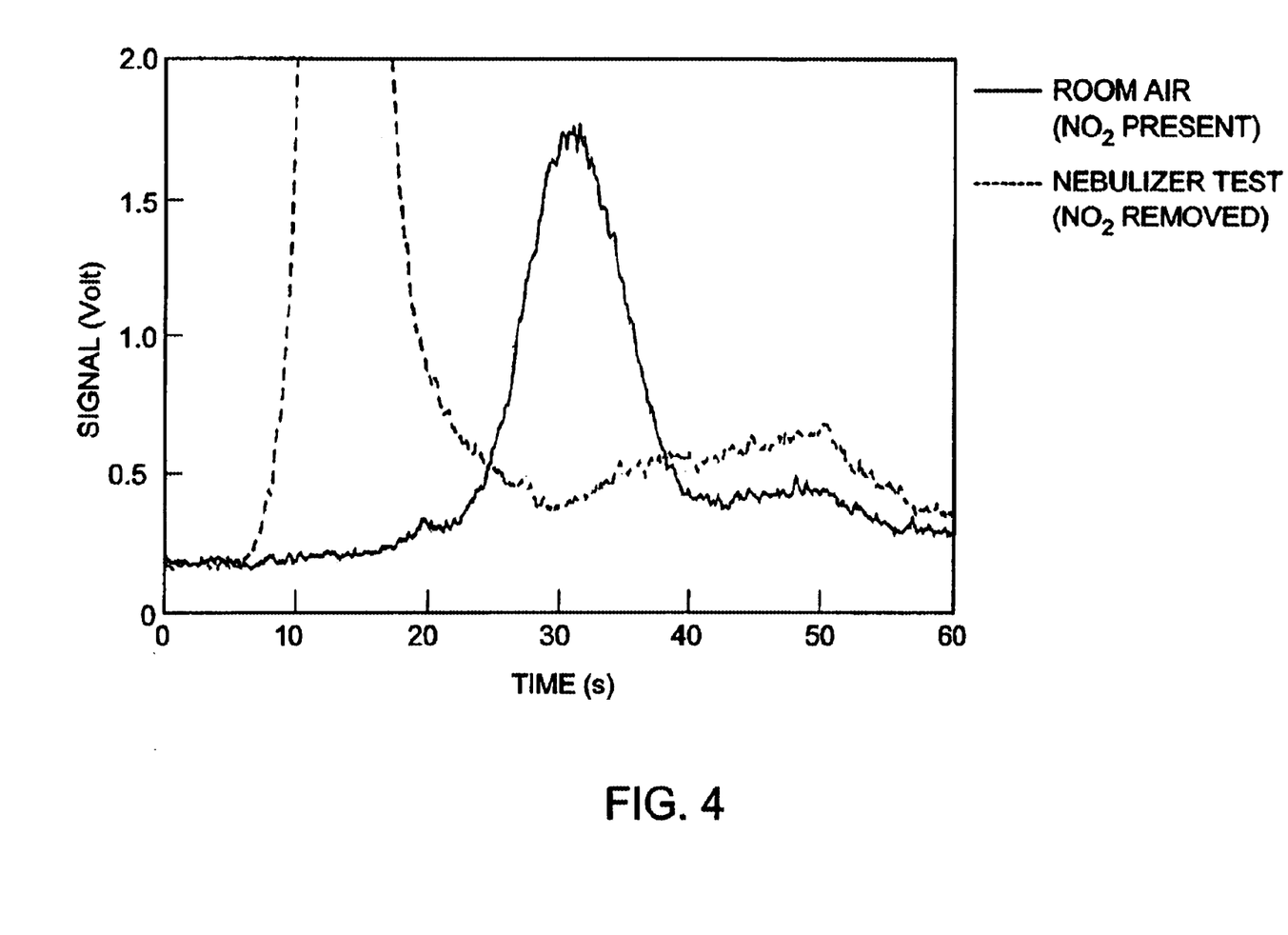
FIG. 4 demonstrates a method of distinguishing between nitrate and $NO_2$ in a sample of gas using the systems and methods described herein.

FIG. 4 illustrates how $NO_2$ in the gas sample as collected and $NO_2$ released from volatilization of nitrate particles can be distinguished using the present method, even in the absence of an extractor.

Figure 5A:
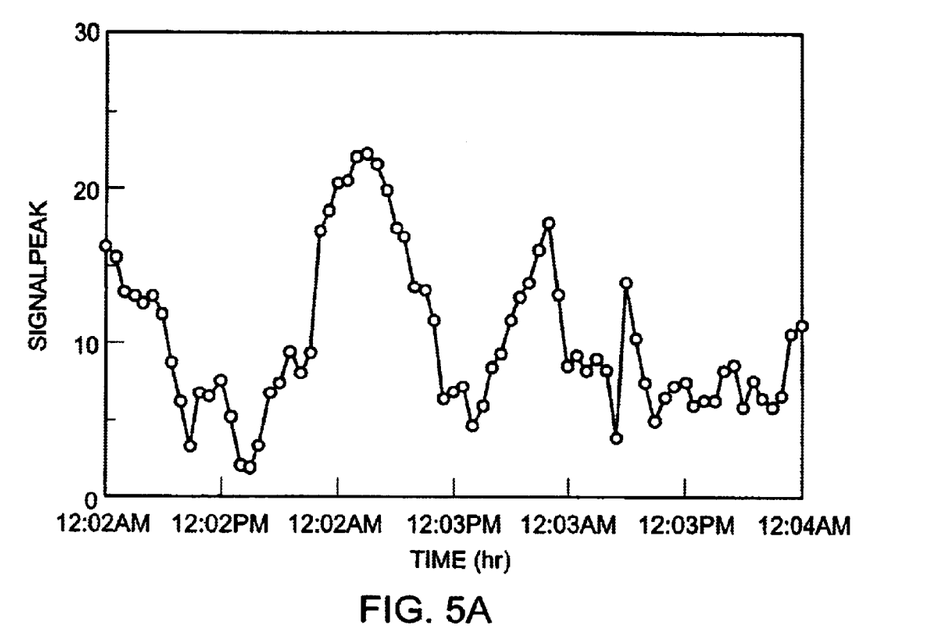
FIGS. 5A and B present nitrate measurement results obtained over a 72-hour period.
Figure 5B:
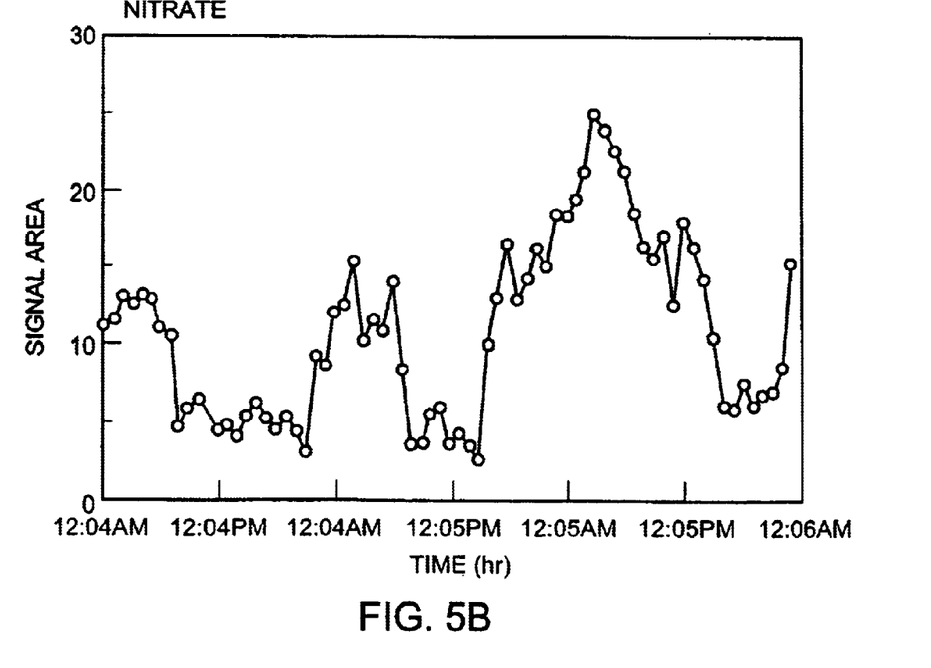

FIGS. 5A and 5B present data collected from atmospheric air samples over three-day periods. Considerable variation can be seen within a given 24-hour period, and these variations can be elucidated because of the relatively short collection-analysis cycles possible using the systems and methods disclosed above.

All articles, patents, and other references set forth above are hereby incorporated by reference. While the invention has been disclosed in connection with the embodiments shown and described in detail, various equivalents, modifications, and improvements will be apparent to one of ordinary skill in the art from the above description. Such equivalents, modifications, and improvements are intended to be encompassed by the following claims.

What is claimed is:

1. A system for measuring nitrate levels, comprising
   a first inlet for receiving a sample of gas,
   a collection body coupled to said first inlet,
   a filter mounted within said body, said filter interposed in the path of said sample of gas to collect particles from said sample of gas,
   a heater coupled to the body to heat the filter to volatilize the particles collected on the filter
   a cooling system coupled to the body to cool the collection body,
   a second inlet coupled to said body to provide a flow of gas through said body, an outlet for delivering said sample of gas from said collection body and
   a detector coupled to the outlet of said body to measure an $NO_x$ concentration.

2. The system of claim 1, further comprising
   a source of gas coupled to said second inlet.

3. The system of claim 2, wherein said gas is nitrogen.

4. The system of claim 2, wherein said gas is substantially free of oxygen.

5. The system of claim 1, further comprising
   a catalyst, coupled to said body and to said detector, capable of reducing $NO_2$ to NO.

6. The system of claim 5, wherein said catalyst comprises molybdenum.

7. The system of claim 1, wherein said detector includes a light sensor.

8. The system of claim 7, wherein said detector further includes an ozone generator.

9. The system of claim 1, wherein said detector includes an infrared sensor.

10. The system of claim 1, wherein said detector includes a material which reversibly binds NO.

11. The system of claim 1, wherein said filter comprises quartz fibers.

12. The system of claim 1, further comprising
    an extractor coupled to said first inlet and to said collection body to substantially remove $NO_2$ from the gas sample.

13. The system of claim 12, wherein the extractor comprises a hydroxyl-bearing solvent and a base.

14. The system of claim 12, further comprising
    a selection platform, situated between said first inlet and said extractor, to substantially remove particles larger than about 2.5 microns.

15. The system of claim 14, wherein said selection platform is a filter.

16. The system of claim 14, wherein said selection platform is an inertial impactor.

17. A system for measuring nitrate levels, comprising
    a sample inlet to receive a sample of gas,
    an extractor coupled to said sample inlet to substantially remove $NO_2$ from the gas sample,
    a collection body coupled to said sample inlet,
    an inertial impactor mounted within said body, said inertial impactor interposed in the path of said sample of gas to collect particles from the gas sample,
    a heater coupled to the body to heat the inertial impactor to volatilize the particles collected on the inertial impactor,
    a current source coupled to the inertial impactor to heat the inertial impactor and generate $NO_x$,
    a cooling system coupled to the body to cool the collection body, and
    a detector coupled to a catalyst to measure an $NO_x$ concentration.

* * * * *